US00PP22833P2

(12) United States Plant Patent
Pieters

(10) Patent No.: US PP22,833 P2
(45) Date of Patent: Jul. 3, 2012

(54) *CHRYSANTHEMUM* PLANT NAMED 'AMIKO WHITE'

(50) Latin Name: *Chrysanthemum×morifolium*
Varietal Denomination: Amiko White

(75) Inventor: Dirk Pieters, Oostnieuwkerke (BE)

(73) Assignee: Paraty B.V.B.A., Oostnieuwkerke ( * ) Notice: Subject to any disclaimer, the term of this patent is extended or adjusted under 35 U.S.C. 154(b) by 0 days.

(21) Appl. No.: 13/065,895

(22) Filed: Mar. 31, 2011

(51) Int. Cl.
*A01H 5/00* (2006.01)

(52) U.S. Cl. ..... Plt./288

(58) Field of Classification Search ..... Plt./288
See application file for complete search history.

*Primary Examiner* — Kent L Bell
(74) *Attorney, Agent, or Firm* — C. A. Whealy

(57) ABSTRACT

A new and distinct cultivar of *Chrysanthemum* plant named 'Amiko White', characterized by its compact, upright, outwardly spreading and rounded plant habit; freely branching habit; dense and full plant habit; uniform and freely flowering habit; decorative-type inflorescences with white-colored ray florets that are initially light yellow in color; and excellent garden performance.

1 Drawing Sheet

Botanical designation: *Chrysanthemum×morifolium.*
Cultivar denomination: 'AMIKO WHITE'.

CROSS-REFERENCED TO CLOSELY RELATED APPLICATIONS

Title: *Chrysanthemum* Plant Named 'Amiko Yellow'.
Applicant: Dirk Pieters.
Filed: U.S. Plant patent application Ser. No. 13/065,899.

BACKGROUND OF THE INVENTION

The present invention relates to a new and distinct cultivar of *Chrysanthemum* plant, botanically known as *Chrysanthemum×morifolium*, and hereinafter referred to by the name 'Amiko White'.

The new *Chrysanthemum* is a naturally-occurring whole plant mutation of *Chrysanthemum×morifolium* 'Amiko Violet', not patented. The new *Chrysanthemum* plant was discovered and selected by the Inventor as a flowering plant from within a population of plants of 'Amiko Violet' in a controlled greenhouse environment in Oostnieuwkerke, Belgium in September, 2007.

Asexual reproduction of the new *Chrysanthemum* plant by vegetative cuttings was first conducted in a controlled greenhouse environment in Oostnieuwkerke, Belgium in January, 2008. Asexual reproduction by cuttings has shown that the unique features of this new *Chrysanthemum* plant are stable and reproduced true to type in successive generations.

SUMMARY OF THE INVENTION

Plants of the new *Chrysanthemum* have not been observed under all possible environmental conditions and cultural conditions. The phenotype may vary somewhat with variations in environment such as temperature, daylength and light intensity, without, however, any variance in genotype.

The following traits have been repeatedly observed and are determined to be the unique characteristics of 'Amiko White'. These characteristics in combination distinguish 'Amiko White' as a new and distinct *Chrysanthemum* plant:

1. Compact, upright, outwardly spreading and rounded plant habit.
2. Freely branching habit; dense and full plant habit.
3. Uniform and freely flowering habit.
4. Decorative-type inflorescences with white-colored ray florets that are initially light yellow in color.
5. Excellent garden performance.

Plants of the new *Chrysanthemum* differ primarily from the parent, 'Amiko Violet', in ray floret color as plants of 'Amiko Violet' have violet-colored ray florets.

Plants of the new *Chrysanthemum* differ primarily from the *Chrysanthemum×morifolium* 'Amiko Yellow', disclosed in U.S. Plant patent application Ser. No. 13/065,899, in ray floret color as plants of 'Amiko Yellow' have bright yellow-colored ray florets.

Plants of the new *Chrysanthemum* can also be compared to plants of *Chrysanthemum×morifolium* 'PPP ALUG 09', disclosed in U.S. Plant Pat. No. 21,454. In side-by-side comparisons conducted in Oostnieuwkerke, Belgium, plants of the new *Chrysanthemum* differed from plants of 'PPP ALUG 09' in the following characteristics:

1. Plants of the new *Chrysanthemum* were more compact than plants of 'PPP ALUG 09'.
2. Plants of the new *Chrysanthemum* had lighter green-colored leaves than plants of 'PPP ALUG 09'.

BRIEF DESCRIPTION OF THE PHOTOGRAPH

The accompanying photograph illustrates the overall appearance of the new *Chrysanthemum* plant showing the colors as true as it is reasonably possible to obtain in colored reproductions of this type. Colors in the photograph may differ slightly from the color values cited in the detailed botanical description which accurately describe the colors of the new *Chrysanthemum* plant.

The photograph comprises a side perspective view of a typical flowering plant of 'Amiko White' grown in a container.

DETAILED BOTANICAL DESCRIPTION

The aforementioned photograph and following observations and measurements describe plants grown in 19-cm containers in an outdoor nursery in Oostnieuwkerke, Belgium during the summer and autumn and under conditions and practices which approximate those generally used in commercial *Chrysanthemum* production. During the production of the plants, day temperatures ranged from 25° C. to 30° C. and night temperatures ranged from 15° C. to 20° C. Plants were 20 weeks old when the photograph and description were taken. In the following description, color references are made to The Royal Horticultural Society Colour Chart, 2005 Edition, except where general terms of ordinary dictionary significance are used.

Botanical classification: *Chrysanthemum×morifolium* 'Amiko White'.

Parentage: Naturally-occurring whole plant mutation of *Chrysanthemum×morifolium* 'Amiko Violet', not patented.

Propagation:

*Type*.—Terminal vegetative cuttings.

*Time to initiate roots, summer*.—About 14 days at temperatures of about 20° C.

*Time to initiate roots, winter*.—About 20 days at temperatures of about 20° C.

*Time to produce a rooted young plant, summer*.—About 30 days at temperatures of about 20° C.

*Time to produce a rooted young plant, winter*.—About 40 days at temperatures of about 20° C.

*Root description*.—Fine, fibrous; light brown in color.

*Rooting habit*.—Freely branching; moderately dense.

Plant description:

*Appearance*.—Perennial decorative-type *Chrysanthemum*; compact plant habit with stems upright and outwardly spreading giving a uniformly rounded appearance to the plant; very freely branching habit, about 20 primary lateral branches develop, each primary lateral branch with multiple secondary branches; pinching enhances lateral branch development; dense and full plant habit; moderately vigorous growth habit.

*Plant height*.—About 45 cm.

*Plant width*.—About 50 cm.

*Lateral branches*.—Length: About 20 cm to 22 cm. Diameter: About 2 mm to 3 mm. Internode length: About 4 cm. Strength: Strong. Texture: Pubescent; longitudinally ridged. Color: Close to 145A.

*Leaves*.—Arrangement: Alternate, simple. Length: About 2.5 cm to 4 cm. Width: About 2.5 cm to 3 cm. Apex: Rounded to cuspidate. Base: Attenuate. Margin: Palmately lobed and serrate, sinuses between lateral lobes divergent to parallel. Texture, upper and lower surfaces: Slightly pubescent. Color: Developing leaves, upper surface: Close to 145A. Developing leaves, lower surface: Close to 145B. Fully expanded leaves, upper surface: Close to 139C; venation, close to 148C. Fully expanded leaves, lower surface: Close to 145B; venation, close to 147B to 147C. Petiole: Length: About 1 cm. Diameter: About 2 mm. Texture, upper and lower surfaces: Slightly pubescent and rough. Color, upper surface: Close to 139C. Color, lower surface: Close to 145B.

Inflorescence description:

*Appearance*.—Decorative-type inflorescence form; inflorescences borne on terminals above foliar plane; disc and ray florets arranged acropetally on a capitulum.

*Fragrance*.—Faintly fragrant, pungent.

*Flowering response*.—Under natural season conditions, plants flower mid-September in Belgium; flowering response time, about six weeks.

*Postproduction longevity*.—Inflorescences maintain good color and substance for about seven weeks in an outdoor nursery; inflorescences persistent.

*Quantity of inflorescences*.—About 20 inflorescences develop per lateral branch.

*Inflorescence bud*.—Height: About 2 cm. Diameter: About 2.5 cm. Shape: Globular. Color: Close to 145A.

*Inflorescence size*.—Diameter: About 7 cm. Depth (height): About 4 cm. Disc diameter: About 3 mm. Receptacle diameter: About 3 mm. Receptacle height: About 2.5 mm to 3 mm. Receptacle color: Close to 144B.

*Ray florets*.—Length: About 5 cm to 7 cm. Width: About 7 mm. Shape: Oval. Apex: Rounded. Base: Attenuate. Margin: Entire. Aspect: Mostly flat. Texture, upper and lower surfaces: Smooth, glabrous. Number of ray florets per inflorescence: About 150 to 200 arranged in about ten whorls. Color: When opening, upper and lower surfaces: Close to 4D. Fully opened, upper and lower surfaces: Close to 155B; color becoming closer to 155D with development.

*Disc florets*.—Length: About 3 mm. Diameter: About 0.5 mm to 1 mm. Shape: Tubular, elongated; apices acute. Number of disc florets per inflorescence: About 30 massed at the center of the inflorescence. Color, immature: Close to 145A. Color, mature: Close to 12A.

*Phyllaries*.—Number of phyllaries per inflorescence: About 25 arranged in two or three whorls. Length: About 4 mm to 6 mm. Width: About 2 mm to 3 mm. Shape: Ovate. Apex: Rounded. Base: Rounded to truncate. Margin: Entire. Texture, upper and lower surfaces: Smooth, glabrous. Color, upper surface: Close to 137A. Color, lower surface: Close to N137B.

*Peduncles*.—Length, terminal peduncle: About 3 cm. Length, fourth peduncle: About 4 cm. Length, seventh peduncle: About 5 cm. Diameter: About 4 mm. Angle: About 30° from vertical. Strength: Moderately strong. Texture: Slightly pubescent. Color: Close to 145A.

*Reproductive organs*.—Androecium: Not observed. Gynoecium: Not observed.

*Seed/fruit*.—Seed and fruit production have not been observed.

Disease/pest resistance: Resistance to pathogens and pests common to *Chrysanthemums* has not been observed on plants grown under commercial conditions.

Garden performance: Plants of the new *Chrysanthemum* have demonstrated excellent garden performance and will tolerate temperatures ranging from about 0° C. to about 45° C.

It is claimed:

1. A new and distinct *Chrysanthemum* plant named 'Amiko White' as illustrated and described.

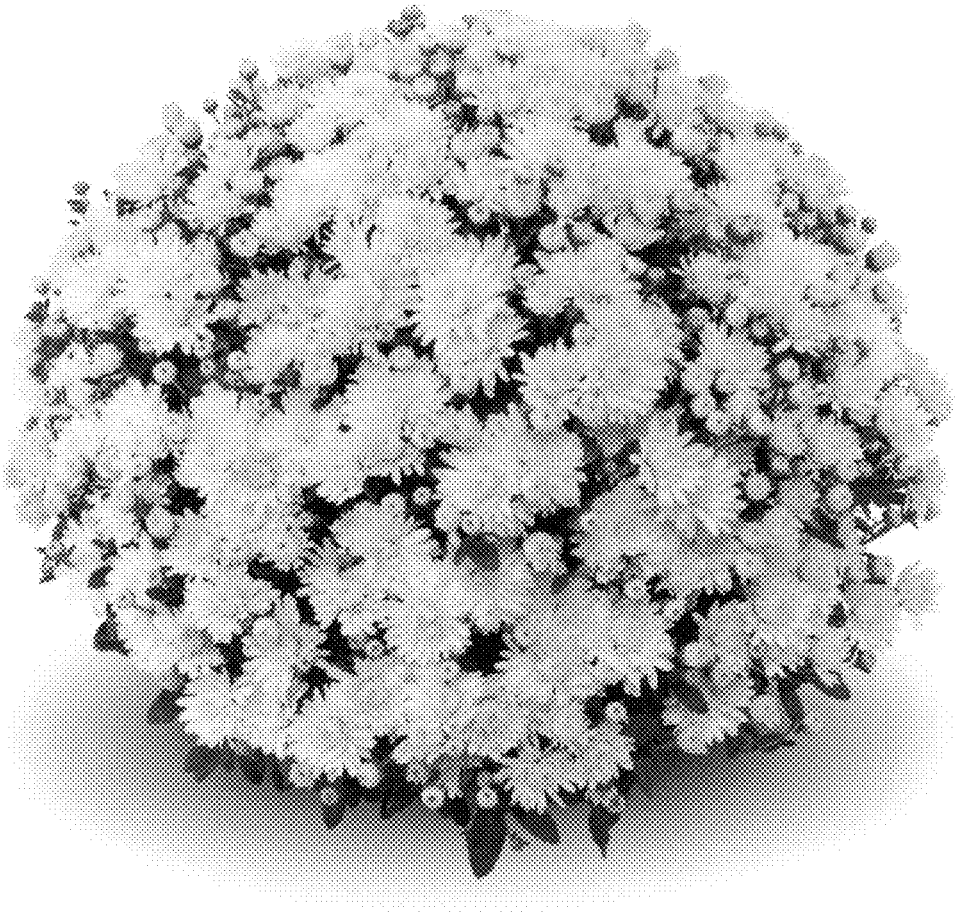

* * * * *